US012564488B2

(12) United States Patent
Mazzawi

(10) Patent No.: US 12,564,488 B2
(45) Date of Patent: Mar. 3, 2026

(54) OSSICULAR REPLACEMENT PROTHESIS WITH CONTROLLABLE STAPEDIAL CONFORMING FUNCTION, MANUFACTURE METHOD THEREOF AND APPLICATOR DEVICE THEREFOR

(71) Applicant: J.N. MEDICAL, Nazareth (IL)

(72) Inventor: Salim Mazzawi, Nazareth (IL)

(73) Assignee: J.N. MEDICAL, Nazareth (IL)

( * ) Notice: Subject to any disclaimer, the term of this patent is extended or adjusted under 35 U.S.C. 154(b) by 816 days.

(21) Appl. No.: 17/886,967

(22) Filed: Aug. 12, 2022

(65) Prior Publication Data

US 2023/0049803 A1 Feb. 16, 2023

(30) Foreign Application Priority Data

Aug. 12, 2021 (IL) ......................................... 285583

(51) Int. Cl.
*A61F 2/18* (2006.01)
*A61B 17/34* (2006.01)
*A61F 2/00* (2006.01)

(52) U.S. Cl.
CPC ............ *A61F 2/18* (2013.01); *A61B 17/3468* (2013.01); *A61F 2002/0081* (2013.01);
(Continued)

(58) Field of Classification Search
CPC . A61B 17/3468; A61B 17/0469; A61B 1/227; A61F 2002/183; A61F 11/04; A61F 11/06; A61F 11/20; A61F 11/30
See application file for complete search history.

(56) References Cited

U.S. PATENT DOCUMENTS

| 6,168,625 | B1 | 1/2001 | Prescott |
| 7,087,081 | B2 | 8/2006 | Prescott et al. |

(Continued)

FOREIGN PATENT DOCUMENTS

| DE | 19845906 A1 | 4/1999 |
| EP | 2583639 | 4/2013 |

(Continued)

OTHER PUBLICATIONS

The Israel Patent Office Search Report dated Nov. 15, 2021, issued in the corresponding Israel Patent Application No. 285583, now Patent No. 285583.

(Continued)

*Primary Examiner* — Melanie R Tyson
*Assistant Examiner* — Paris Marie Blass
(74) *Attorney, Agent, or Firm* — Mark S. Cohen; PEARL COHEN ZEDEK LATZER BARATZ LLP

(57) ABSTRACT

A system for partial ossicular replacement with controllable stapedial engaging function is described; a respective process of manufacturing a partial ossicular replacement prosthesis with controllable stapedial engaging function and a partial ossicular replacement prosthesis are further described; the system comprises: a partial ossicular replacement prosthesis comprising a stapedial part and a tympanic part, an applicator device comprising a handpiece, an essentially planar static face, an elongated essentially cylindrically shaped plunger; the process comprises: providing a preform of at least stapedial part, forming a plurality of elongated cuts, shaping a centrical portion, shaping a distal portion; the partial ossicular replacement prosthesis comprises a stapedial part and a tympanic part.

19 Claims, 11 Drawing Sheets

(52) U.S. Cl.
 CPC . *A61F 2002/183* (2013.01); *A61F 2220/0033*
 (2013.01); *A61F 2230/0004* (2013.01); *A61F*
 *2230/0069* (2013.01); *A61F 2240/001*
 (2013.01); *A61F 2250/0007* (2013.01); *A61F*
 *2250/001* (2013.01); *A61F 2250/0039*
 (2013.01)

(56)                    References Cited

U.S. PATENT DOCUMENTS

|  |  |  |
|---|---|---|
| 8,192,489 B2 | 6/2012 | Edwards |
| 8,206,444 B2 | 6/2012 | Reitan |
| 8,936,637 B2 | 1/2015 | Steinhardt et al. |
| 10,595,990 B2 | 3/2020 | Fjord et al. |
| 10,646,331 B2 | 5/2020 | Hirsch et al. |
| 2008/0097602 A1 | 4/2008 | Brosnahan et al. |
| 2009/0149697 A1 | 6/2009 | Steinhardt |
| 2010/0191331 A1 | 7/2010 | Steinhardt et al. |
| 2016/0175093 A1 | 6/2016 | Babu et al. |
| 2019/0192425 A1 | 6/2019 | Lichter et al. |
| 2019/0201189 A1 | 7/2019 | Steinhardt et al. |

FOREIGN PATENT DOCUMENTS

|  |  |  |
|---|---|---|
| WO | 1992018066 | 10/1992 |
| WO | WO-1998016175 A1 | 4/1998 |

OTHER PUBLICATIONS

The Extended European Search Report dated Jan. 18, 2023, issued
in the corresponding European Patent Application No. EP 22189745.
7, now Patent No. EP 4134045.

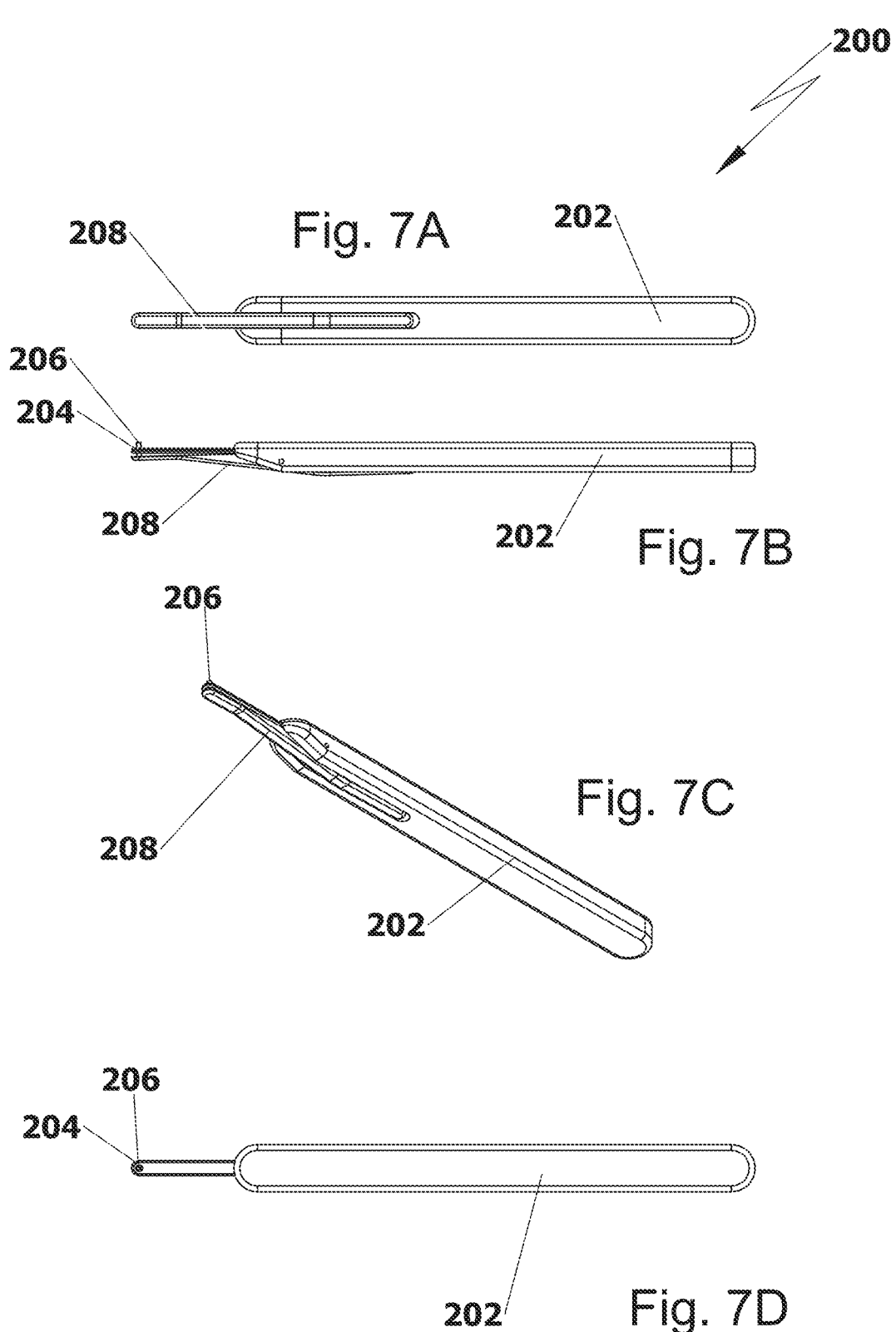
200
208     Fig. 7A     202
206
204
208     202     Fig. 7B
206
208     Fig. 7C
202
206
204
202     Fig. 7D

OSSICULAR REPLACEMENT PROTHESIS WITH CONTROLLABLE STAPEDIAL CONFORMING FUNCTION, MANUFACTURE METHOD THEREOF AND APPLICATOR DEVICE THEREFOR

TECHNICAL FIELD

In general, the present invention pertains to the art of medical devices. In particular, the invention relates to partial ossicular replacement prosthesis with controllable stapedial conforming function, manufacture method thereof and applicator device.

BACKGROUND ART

Ossiculoplasty reconstructs a sound-conducting mechanism between the tympanic membrane (TM) graft and oval window. The surgery performed is dependent on the ossicular deficit. Variations include the use of a prosthesis, autologous ossicle (most commonly the incus), bone cement, cartilage, etc. In general terms, a partial ossicular replacement prosthesis (PORP) extends from the tympanic membrane (TM), malleus, or incus to an intact stapes with mobile footplate.

A total ossicular replacement prosthesis (TORP) replaces the entire ossicular chain while a partial ossicular replacement prosthesis (PORP) replaces only the incus and malleus but not the stapes. Indications for use of an ossicular replacement prosthesis include: chronic middle ear disease, otosclerosis, congenital fixation of the stapes, secondary surgical intervention to correct for a significant and persistent conductive hearing loss from prior otologic surgery, as well as surgically correctable injury to the middle ear from trauma.

It is believed that the current state of the art is represented by the following patent literature: U.S. Pat. Nos. 6,168,625, 7,087,081, 8,192,489, 8,206,444, 8,936,637, 10,646,331, US20090149697, US2019201189, US2019192425, EP2583639 and WO1992018066.

U.S. Pat. No. 8,206,444 describes a middle ear prosthesis comprising a body of deformable material capable of retaining different shapes. The body in U.S. Pat. No. 8,206,444 comprises a slotted wall defining a cavity for receiving a bone of the middle ear. The wall in U.S. Pat. No. 8,206,444 is deformable, proximate slots in the wall between an open position for receiving the bone and a closed position wherein the body is reshaped to grasp the bone.

U.S. Pat. No. 7,087,081 describes a stapedial prosthesis includes a body defining a bucket and a shaft, and a bail handle coupled to the bucket and a method of implanting a stapedial prosthesis. The bucket in U.S. Pat. No. 7,087,081 is preferably adjustable in diameter to fit the incus lenticular process. The shaft in U.S. Pat. No. 7,087,081 preferably has a varying diameter, with a central portion of a smaller diameter than a distal portion which aids in depth perception during implantation and reduces mass to permit better sound energy transmission by the prosthesis. The bail handle in U.S. Pat. No. 7,087,081 is preferably spring-loaded and preferably constructed of titanium. The bail handle in U.S. Pat. No. 7,087,081 may be coupled to the body without crimping, twisting or welding and preferably biases the incus toward the bucket.

SUMMARY OF THE INVENTION

The following summary of the invention is provided in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

The invention was made in view of the deficiencies of the prior art and provides systems, methods and processes for overcoming these deficiencies. According to some embodiments and aspects of the present invention, there are provided a partial ossicular replacement prostheses with controllable stapedial conforming function, methods of manufacturing the partial ossicular replacement prostheses with controllable stapedial conforming function, applicator devices for the partial ossicular replacement prostheses with controllable stapedial conforming function and methods of operating the applicator devices for the partial ossicular replacement prostheses with controllable stapedial conforming function.

In accordance with some aspects and embodiments of the present invention a system is provided for partial ossicular replacement with controllable stapedial engaging portion function includes: a partial ossicular replacement prosthesis including: a stapedial part including an essentially cylindrical shell shape with an elongated interior lumen, the stapedial part including: a distal terminal stapedial engaging portion including a plurality of structured elements configured for controllably conforming to a distal portion of a stapes; a centrical applicator operated portion, forming a continuum with the stapedial engaging portion, including a plurality of protruding elements facing inwardly into the elongated interior lumen of the stapedial part, in which the plurality of protruding elements are configured to be operated by an applicator; a proximal basal stem portion, forming a continuum with the centrical portion; a tympanic part including an essentially flattened shape, the tympanic part including: an anterior face, associated with a tympanic membrane; a posterior face, forming a continuum with the proximal basal stem portion; a throughout aperture, disposed essentially at a center of the essentially flattened shape; an applicator device for the partial ossicular replacement prosthesis including: a handpiece configured for manual grip by an operator; an essentially planar static face, configured to engage to the anterior face of the tympanic part of the partial ossicular replacement prosthesis; an elongated essentially cylindrically shaped plunger, configured to be introducible into the elongated interior lumen of the stapedial part of the partial ossicular replacement prosthesis, through the throughout aperture in the tympanic part of the partial ossicular replacement prosthesis; a tab operatively connected to the elongated essentially cylindrically shaped plunger, configured for controllably translating the essentially cylindrically shaped plunger within the elongated interior lumen of the stapedial part of the partial ossicular replacement prosthesis; in which the partial ossicular replacement prosthesis is configured to assume at least two configurations: a divergent configuration in which a distal portion of the plunger is engaged to the plurality of protruding elements of the centrical portion of the stapedial part; whereby the plurality of the structured elements of the distal terminal stapedial engaging portion of the stapedial part are essentially spread apart, and a convergent configuration in which the distal portion of the plunger is withdrawn from the plurality of protruding elements of the centrical portion of the stapedial part; whereby the plurality of the structured elements of the distal terminal stapedial engaging portion of the stapedial part essentially conform to the distal portion of the stapes.

In some embodiments, the partial ossicular replacement prosthesis is configured to assume a plurality of configurations in-between the divergent configuration and the convergent configuration.

In some embodiments, the plunger is configured to be controllably withdrawn within the elongated interior lumen of the stapedial part, whereby the partial ossicular replacement prosthesis is configured to be gradually altered between the divergent and the convergent configurations.

In some embodiments, the partial ossicular replacement prosthesis includes at least one biocompatible material selected from a group of: a pliable or pliant metal, pliable or pliant alloy, bio-ceramic material, plastic resilient and any combination thereof.

In some embodiments, a prostheses kit including a plurality of the partial ossicular replacement prostheses is provided, in which the essentially cylindrical shell shape with the elongated interior lumen of the stapedial part of each one of the plurality of the partial ossicular replacement prostheses includes at least one different parameter of: a length, diameter and shape.

In some embodiments, at least one edge of the plurality of structured elements of the stapedial engaging portion of the stapedial part of the partial ossicular replacement prosthesis includes a profile selected from a group of: a chamfered profile, filleted profile or beveled profile.

In some embodiments, the tympanic part of the partial ossicular replacement prosthesis includes at least one shape selected from a group of: a discoid shape, egg shape, oval shape, bulb shaped and horseshoe shape.

In some embodiments, the tympanic part of the partial ossicular replacement prosthesis includes at least one structural element selected from a group of: a notch, groove, recess, circular aperture, structured aperture, furrowed surface and textured surface.

In some embodiments, the proximal basal stem portion of the stapedial part of the partial ossicular replacement prosthesis includes external screw threading matching an internal screw threading of the throughout aperture of the tympanic part of the partial ossicular replacement prosthesis, in which the stapedial part of the partial ossicular replacement is configured for length adjustment.

In some embodiments, the plunger forms a perpendicular arrangement with the tab of the applicator device for the partial ossicular replacement prosthesis.

In accordance with some aspects and embodiments of the present invention a process of manufacturing a partial ossicular replacement prosthesis with controllable stapedial engaging function is provided, including the steps of: providing a preform of at least stapedial part including an essentially cylindrical shell shape with an elongated interior lumen; forming a plurality of elongated cuts from a terminal distal face of the stapedial part preform, along a substantial length of the essentially cylindrical shell shape, thereby forming a plurality of elongated biasing elements, extending from a proximal basal stem portion of the essentially cylindrical shell shape; shaping the a centrical portion of the plurality of elongated biasing elements to form a plurality of protruding elements facing inwardly into the elongated interior lumen, thereby forming a centrical applicator operated portion of the stapedial part; thereby forming at least a stapedial part of the partial ossicular replacement prosthesis.

In some embodiments, the process of manufacturing a partial ossicular replacement prosthesis further includes shaping a distal terminal portion of the plurality of the plurality of elongated biasing elements to form a plurality of structured elements configured to conform to a distal portion of a stapes, thereby forming a stapedial engaging portion of the stapedial part.

In some embodiments, the process of manufacturing a partial ossicular replacement prosthesis further includes shaping an edge of at least one distal terminal portion of the plurality of elongated biasing elements to form a profile selected from a group of: a chamfered profile, filleted profile or beveled profile.

In some embodiments, the process of manufacturing a partial ossicular replacement prosthesis further includes connecting a tympanic part to the stapedial part, thereby forming the partial ossicular replacement prosthesis.

In some embodiments, the process of manufacturing a partial ossicular replacement prosthesis further includes forming a throughout aperture, essentially at a center of the tympanic part of the partial ossicular replacement prosthesis.

In some embodiments, the process of manufacturing a partial ossicular replacement prosthesis further includes forming a plurality of marquise shaped recesses in-between the elongated biasing elements, following the step of forming a plurality of the elongated cuts from a terminal distal face of the stapedial part preform and preceding the step of shaping the a centrical portion of the plurality of the elongated biasing elements.

In accordance with some aspects and embodiments of the present invention a partial ossicular replacement prosthesis with controllable stapedial engaging function is provided, including: a stapedial part including: a distal terminal stapedial engaging portion including a plurality of structured elements configured for controllably conforming to a distal portion of a stapes and a centrical applicator operated portion, forming a continuum with the stapedial engaging portion, including a plurality of protruding elements facing inwardly into the elongated interior lumen of the stapedial part, in which the plurality of protruding elements are configured to be operated by an applicator; a proximal basal stem portion, forming a continuum with the centrical portion; a tympanic part including an essentially flattened shape, the tympanic part including: an anterior face, associated with a tympanic membrane; a posterior face, forming a continuum with the proximal basal stem portion; a throughout aperture, disposed essentially at a center of the essentially flattened shape; in which the partial ossicular replacement prosthesis is configured to assume at least two configurations: a divergent configuration in which a distal portion of a plunger of the applicator is engaged to the plurality of protruding elements of the centrical portion of the stapedial part; whereby the plurality of the structured elements of the distal terminal stapedial engaging portion of the stapedial part are essentially spread apart, and a convergent configuration in which the distal portion of the plunger of the applicator is withdrawn from the plurality of protruding elements of the centrical portion of the stapedial part; whereby the plurality of the structured elements of the distal terminal stapedial engaging portion of the stapedial part essentially conform to the distal portion of the stapes.

In some embodiments, the partial ossicular replacement prosthesis is configured to assume a plurality of configurations in-between the divergent configuration and the convergent configuration.

In accordance with some aspects and embodiments of the present invention a method of operating an applicator device for a partial ossicular replacement prosthesis with controllable stapedial engaging function is provided including: providing a partial ossicular replacement prosthesis including: a stapedial part including an essentially cylindrical shell shape with an elongated interior lumen, the stapedial part including: a distal terminal stapedial engaging including a plurality of structured elements configured for controllably conforming to a distal portion of a stapes; a centrical applicator operated portion, forming a continuum with the stapedial engaging portion, including a plurality of protruding elements facing inwardly into the elongated interior lumen of the stapedial part; a proximal basal stem portion, forming a continuum with the centrical portion; a tympanic part including an essentially flattened shape, the tympanic part including: an anterior face, associated with a tympanic membrane; a posterior face, forming a continuum with the proximal basal stem portion; a throughout aperture, disposed essentially at a center of the essentially flattened shape; in which the partial ossicular replacement prosthesis is configured to assume at least two configurations: a divergent configuration in which a distal portion of a plunger is engaged to the plurality of protruding elements of the centrical portion of the stapedial part; whereby the plurality of the structured elements of the distal terminal stapedial engaging portion of the stapedial part are essentially spread apart, and a convergent configuration in which the distal portion of a plunger is withdrawn from the plurality of protruding elements of the centrical portion of the stapedial part; whereby the plurality of the structured elements of the distal terminal stapedial engaging portion of the stapedial part essentially conform to the distal portion of the stapes; providing an applicator device for a partial ossicular replacement prosthesis with controllable stapedial engaging function including: a handpiece configured for manual grip by an operator; an essentially planar static face, configured to engage to the anterior face of the tympanic part of the partial ossicular replacement prosthesis; an elongated essentially cylindrically shaped plunger, configured to be introducible into the elongated interior lumen of the stapedial part of the partial ossicular replacement prosthesis, through the throughout aperture in the tympanic part of the partial ossicular replacement prosthesis; a tab operatively connected to the elongated essentially cylindrically shaped plunger, configured for controllably translating the essentially cylindrically shaped plunger within the elongated interior lumen of the stapedial part of the partial ossicular replacement prosthesis; introducing the plunger of the applicator device into the elongated interior lumen of the stapedial part of the partial ossicular replacement prosthesis, through the throughout aperture on the tympanic part of the partial ossicular replacement prosthesis; engaging the anterior face of the tympanic part of the partial ossicular replacement prosthesis, to the essentially planar static face of the applicator device; advancing the plunger of the applicator device within the elongated interior lumen of the stapedial part to engage to the plurality of protruding elements of the centrical portion of the stapedial part, thereby driving the partial ossicular replacement prosthesis into the divergent configuration; withdrawing the plunger of the applicator device from the plurality of protruding elements of the centrical portion of the stapedial part, thereby driving the partial ossicular replacement prosthesis into the convergent configuration.

In some embodiments, the method of operating an applicator device further includes displacing the tab of the applicator device, thereby driving the partial ossicular replacement prosthesis to assume a plurality of configurations in-between the divergent configuration and the convergent configuration.

In some embodiments, the method of operating an applicator device further includes controllably withdrawing the plunger within the elongated interior lumen of the stapedial part, thereby gradually altering the partial ossicular replacement prosthesis between the divergent and the convergent configurations.

In some embodiments, the method of operating an applicator device further includes selecting from a prostheses kit including a plurality of the partial ossicular replacement prostheses, a partial ossicular replacement prosthesis, in which the tympanic part of the partial ossicular replacement prosthesis includes at least one shape selected from a group of: a discoid shape, egg shape, oval shape, bulb shaped and horseshoe shape.

In some embodiments, the method of operating an applicator device further includes selecting from a prostheses kit including a plurality of the partial ossicular replacement prostheses, a partial ossicular replacement prosthesis, in which the tympanic part of the partial ossicular replacement prosthesis includes at least one structural element selected from a group of: a notch, groove, recess, circular aperture, structured aperture, furrowed surface and textured surface.

Definitions

The term readily connectable, as referred to herein, should be construed as a standardized unit that may be conveniently connected to other components of the system. The term readily connectable, however, doesn't necessarily means readily disconnectable or removable. The term readily connectable is optionally satisfied by providing for ease of at least onetime connection or coupling.

The terms matching and/or matchable as referred to herein is to be construed as a cross-sectional area and/or shape of a component is equal or essentially similar to a cross-sectional area and/or shape of another component. It should be acknowledged that the component need only to be similar in the cross-sectional areas and/or shapes, to satisfy the term matching/matchable, so long as the cross-sectional areas can be mated or the combination will fit into and/or occupy essentially the same lateral space.

The term structured as referred to herein is to be construed as including any geometrical shape, exceeding in complexity a plain linear shape or a shape embodying simple cylindrical, elliptical or polygonal contour or profile. A more complex shape, a plain linear shape or a shape embodying simple cylindrical, elliptical or polygonal contour or profile, constitutes an example of structured geometry.

The terms firm rigid, or stiff, as referred to herein, are to be construed as having rigidity modulus value, otherwise referred to as the shear modulus, of 4800 MPa or more. Materials are considered to be firm rigid, or stiff but not tensile, when such materials are incapable of being efficiently elastically flexed or bent. Stiff materials, such as steel, are defined as having rigidity modulus value well exceeding 4800 MPa.

The terms pliable or pliant, as referred to herein, are to be construed as having high tensile strength and capable of being efficiently elastically flexed or bent but not being resilient and incapable of being efficiently stretched or expanded. The term tensile or tensile strength, as referred to herein, is to be construed inter alia as a shortcut of the known term ultimate tensile strength, frequently represented acronym as UTS, meaning an intensive property of a material or structure to withstand loads tending to elongate, namely to resist tension, defined as the maximum stress that a material can withstand while been stretched or pulled before sustaining breaking, substantial deformation and/or necking before fracture, such as nylon, relating to essentially non-ductile materials, having UTS value ranging between about 600 and 1000 MPa or more, but not including rigid, firm or stiff materials.

The terms elastic or resilient, as referred to herein, are to be construed as having tensile strength lower than aforesaid tensile strength of pliable or pliant material and optionally being capable of efficiently stretching or expanding, relating inter alia to essentially ductile materials, having UTS value lesser than about 600 MPa.

The term biasing means or alike, as referred to herein, should be construed as including any material, structure or mechanism, configured to accumulate mechanical energy, by changing the configuration thereof, upon a force exerted thereon, such as a compressive, tensile, shear or torsional force, and for releasing the energy accumulated therein, by returning to the normal configuration thereof and by performing a mechanical work, typically by linear or radial displacement. Examples of biasing means in a non-limiting manner include, springs, elastomers, leaf-springs, coil-springs, tension/extension spring, compression spring torsion spring, constant spring, variable spring, variable stiffness spring, flat spring, machined spring, serpentine spring, garter spring, cantilever spring, helical spring, hollow tubing springs, volute spring, V-spring, belleville washer or belleville spring, constant-force spring, gas spring, mainspring, negator spring, progressive rate coil springs, rubber band, spring washer and wave spring.

By operationally connected and operably coupled, as used herein, is meant connected in a specific way (e.g., in a manner allowing water to move and/or electric power to be transmitted) that allows the disclosed system and its various components to operate effectively in the manner described herein.

In the specification or claims herein, any term signifying an action or operation, such as: a verb, whether in base form or any tense, gerund or present/past participle, is not to be construed as necessarily to be actually performed but rather in a constructive manner, namely as to be performed merely optionally or potentially.

The term substantially as used herein is a broad term, and is to be given its ordinary and customary meaning to a person of ordinary skill in the art (and is not to be limited to a special or customized meaning), and refers without limitation to being largely but not necessarily entirely of that quantity or quality which is specified.

The term essentially means that the composition, method or structure may include additional ingredients, stages and or parts, but only if the additional ingredients, the stages and/or the parts do not materially alter the basic and new characteristics of the composition, method or structure claimed.

As used herein, the term essentially changes a specific meaning, meaning an interval of plus or minus ten percent (±10%). For any embodiments disclosed herein, any disclosure of a particular value, in some alternative embodiments, is to be understood as disclosing an interval approximately or about equal to that particular value (i.e., ±10%).

As used herein, the terms about or approximately modify a particular value, by referring to a range equal to the particular value, plus or minus twenty percent (+/−20%). For any of the embodiments, disclosed herein, any disclosure of a particular value, can, in various alternate embodiments, also be understood as a disclosure of a range equal to about that particular value (i.e. +/−20%).

As used herein, the term or is an inclusive or operator, equivalent to the term and/or, unless the context clearly dictates otherwise; whereas the term and as used herein is also the alternative operator equivalent to the term and/or, unless the context clearly dictates otherwise.

It should be understood, however, that neither the briefly synopsized summary nor particular definitions hereinabove are not to limit interpretation of the invention to the specific forms and examples but rather on the contrary are to cover all modifications, equivalents and alternatives falling within the scope of the invention.

DESCRIPTION OF THE DRAWINGS

The present invention will be understood and appreciated more comprehensively from the following detailed description taken in conjunction with the appended drawings in which:

FIG. 7A is a bottom view of the applicator device;

FIG. 7B is a side view of the applicator device;

FIG. 7C is an isometric view of the applicator device;

FIG. 7D is a top view of the applicator device;

Figure 1:
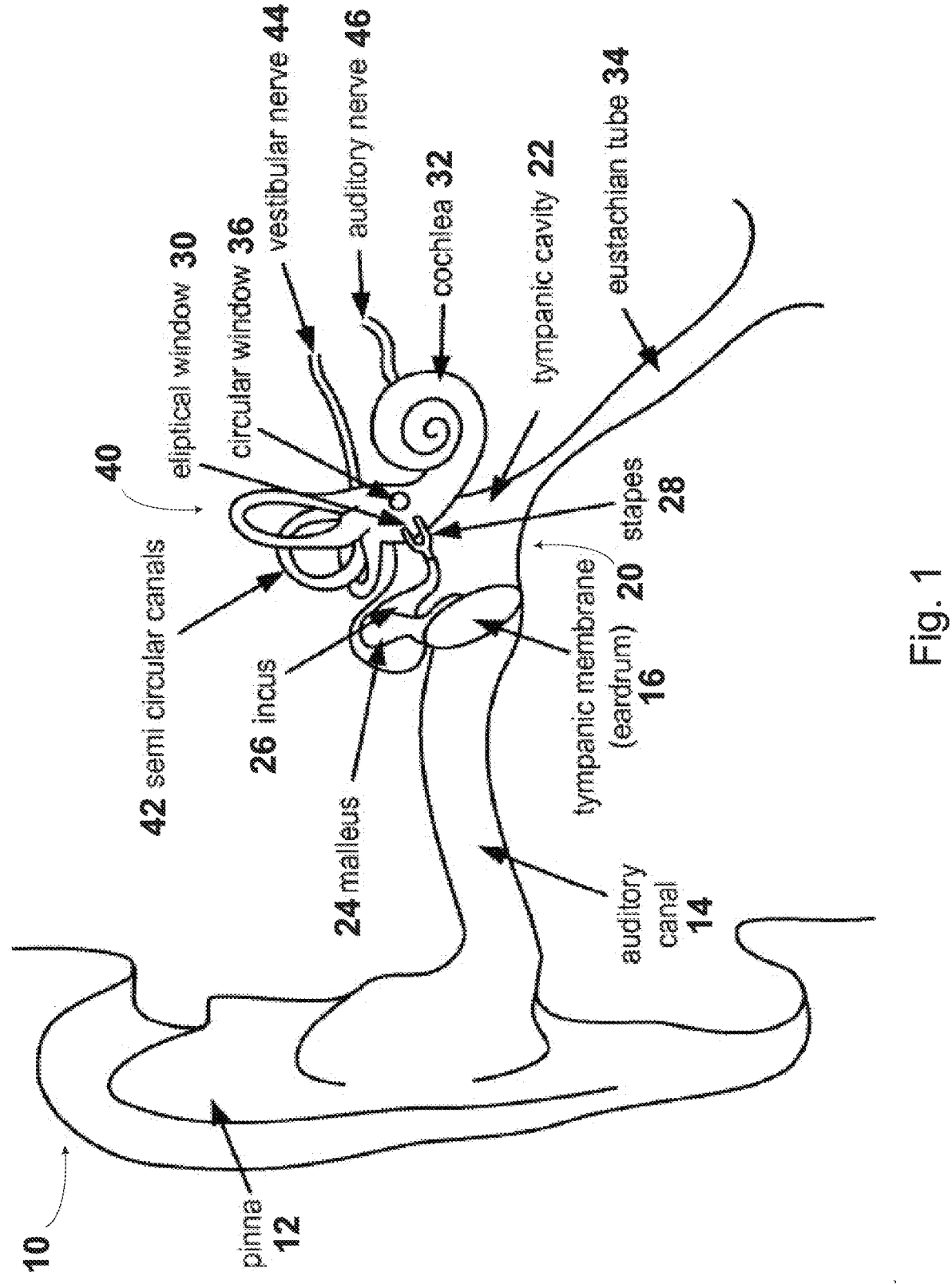
FIG. 1 is a schematic representation of anatomy of the ear.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DESCRIPTION OF THE INVENTION

Prior to elaborating any embodiment of the present invention, in order to present the background for the inventive concept more clearly, reference is firstly made to FIG. 1, showing illustrative representation of anatomy of the ear, shown in FIG. 4 of US20190192425. Outer ear 10 is the external portion of the organ and is composed of pinna (auricle) 12, auditory canal (external auditory meatus) 14 and the outward facing portion of tympanic membrane 16, colloquially known as the ear drum. Pinna 12, which is the fleshy part of outer ear 10 that is visible on the side of the head, collects sound waves and directs them toward auditory canal 14. Tympanic membrane 16, is a thin membrane that separates outer ear 10 from middle ear 20. Thus, the function of outer ear 10, is inter alia to collect and direct sound waves towards tympanic membrane 16 and middle ear 20.

Middle ear 20 is an air-filled tympanic cavity 22, behind tympanic membrane 16. Middle ear 20 lies within the temporal bone, and includes within this space the three ear bones (auditory ossicles): malleus 24, incus 26 and stapes 28. The auditory ossicles are linked together via tiny ligaments, which form a bridge across the space of tympanic cavity 22. Malleus 24 is attached to tympanic membrane 16 at one end, and is linked to incus 26 at its anterior end. Incus 26 is in turn linked to stapes 28. Stapes 28 is attached to oval window 30 (elliptical window), one of two windows located within the tympanic cavity. A fibrous tissue layer, known as the annular stapedial ligament (also called the stapediovestibular joint), forms a ring of fibrous soft tissue that connects the base of the stapes to the oval window of the inner ear.

Sound waves from outer ear 10, first cause tympanic membrane 16 to vibrate. The vibration of tympanic membrane 16 is then transmitted across to cochlea 32 through the auditory ossicles and oval window 30, which transfers the motion to the fluids in auris interna 40. The auditory ossicles are arranged to provide a mechanical linkage between tympanic membrane 16 and oval window 30 of fluid-filled auris interna 40, where sound is transformed and transduced to auris interna 40 for further processing. Stiffness, rigidity or loss of movement of the auditory ossicles, tympanic membrane 16 or oval window 30 leads to hearing loss, e.g. otosclerosis, or rigidity of the stapes bone.

Tympanic cavity 22 also connects to the throat via eustachian tube 34. Eustachian tube 34 provides the ability to equalize the pressure between the outside air and the middle ear cavity. Round window 36 (circular window) is a component of the auris interna 40, which is also accessible within tympanic cavity 22, opens into cochlea 32 of auris interna 40. Round window 36 is covered by a round window membrane, which consists of three layers: an external or mucous layer, intermediate or fibrous layer and internal membrane, which communicates directly with the cochlear fluid. Round window 36, therefore, has direct communication with auris interna 40 via the internal membrane.

Movements in oval 30 and round 36 windows are interconnected, i.e. as stapes 28 bone transmits movement from tympanic membrane 16 to oval window 30 to move inward against the auris interna 40 fluid, round window 36 (round window membrane) is correspondingly pushed out and away from the cochlear fluid. This movement of round window 36 allows movement of fluid within cochlea 32, which leads in turn to movement of the cochlear inner hair cells, allowing hearing signals to be transduced. Stiffness and rigidity in round window 36 membrane leads to hearing loss because of the lack of ability of movement in the cochlear fluid. Recent studies have focused on implanting mechanical transducers onto round window 36, which bypasses the normal conductive pathway through oval window 30 and provides amplified input into the cochlear chamber. By way of example only, some medical device implants bypass damaged portions of the ear and directly stimulate the auditory nerve 46.

Auditory signal transduction takes place in auris interna 40. The fluid-filled auris interna 40, or inner ear, consists of two major components: the cochlear and the vestibular apparatus. Auris interna 40 is located in part within the osseous or bony labyrinth, an intricate series of passages in the temporal bone of the skull. The vestibular apparatus is the organ of balance and consists of the three semi-circular canals 42 and the vestibule. Three semi-circular canals 42 are arranged relative to each other such that movement of the head along the three orthogonal planes in space can be detected by the movement of the fluid and subsequent signal processing by the sensory organs of semi-circular canals 42, called the crista ampullaris. The crista ampullaris contains hair cells and supporting cells, and is covered by a dome-shaped gelatinous mass called the cupula. The hairs of the hair cells are embedded in the cupula. Semi-circular canals 42 detect dynamic equilibrium, the equilibrium of rotational or angular movements.

The endolymph fluid pushes against the cupula, which tilts to one side. As the cupula tilts, it bends some of the hairs on the hair cells of the crista ampullaris, which triggers a sensory impulse. Because each semi-circular canal 42 is located in a different plane, the corresponding crista ampullaris of each semi-circular canal 42 responds differently to the same movement of the head. This creates a mosaic of impulses that are transmitted to the central nervous system on the vestibular branch of vestibulocochlear nerve 44, which mediates the sense of balance and equilibrium.

The vestibule is the central portion of auris interna 40 and contains mechanoreceptors bearing hair cells that ascertain static equilibrium, or the position of the head relative to gravity. Cochlea 32 is the portion of the auris interna 40 related to hearing. Cochlea 32 is a tapered tube-like structure that is coiled into a shape resembling a snail. The inside of cochlea 32 is divided into three regions, which is further defined by the position of the vestibular membrane and the basilar membrane. The portion above the vestibular membrane is the scala vestibuli, which extends from oval window 30 to the apex of cochlea 32 and contains perilymph fluid, an aqueous liquid low in potassium and high in sodium content.

The basilar membrane defines the scala tympani region, which extends from the apex of cochlea 32 to round window 36 and also contains perilymph. The basilar membrane contains stiff fibers, which gradually increase in length from round window 36 to the apex of cochlea 32. The fibers of the basement membrane vibrate when activated by sound. In between the scala vestibuli and the scala tympani is the cochlear duct, which ends as a closed sac at the apex of cochlea 32. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve 44 (cranial nerve VIII).

As discussed, oval window 30, also known as the elliptical window communicates with stapes 28 to relay sound waves that vibrate from tympanic membrane 16. Vibrations transferred to oval window 30 increase the pressure inside fluid-filled cochlea 32 via the perilymph, scala vestibuli and/or scala tympani, which in turn causes round window 36 membrane to expand in response. The concerted inward pressing of the oval window 30 and outward expansion of round window 36 allows for the movement of fluid within cochlea 32 without a change of intra-cochlear pressure. However, as vibrations travel through the perilymph in the scala vestibuli, they create corresponding oscillations in the vestibular membrane.

These corresponding oscillations travel through the endolymph of the cochlear duct and transfer to the basilar membrane. When the basilar membrane oscillates, the organ of Corti moves along with it. The hair cell receptors in the Organ of Corti then move against the tectorial membrane, causing a mechanical deformation in the tectorial membrane. This mechanical deformation initiates the nerve impulse that travels via vestibulocochlear nerve 44 to the central nervous system, mechanically transmitting the sound wave received into signals that are subsequently processed by the central nervous system.

The fragile structures of middle ear 20 are sometimes prone to chronic infections, trauma, or congenital or neoplastic causes, which may damage the auditory ossicles (malleus 24, incus 26 and stapes 28). Discontinuity of bone between tympanic membrane 16 and oval window 30 can lead to a decreased in sound conduction resulting in conductive hearing loss. Conductive hearing loss can be cured by a variety of treatments. Ossiculoplasty reconstructs a sound-conducting mechanism between tympanic membrane 16 and oval window 30. One of the most common treatment procedures is a surgical intervention to remove one or more of the auditory ossicles, when they are entirely or partially absent or damaged, and to replace them with prostheses. These prostheses are called ossicular replacement prostheses (ORP). Ossicular replacement prostheses are used for ossicular reconstruction and for improving sound transmission.

Three types of ossicular replacement prostheses frequently used are: stapes prostheses, partial prostheses (PORP) and total prostheses (TORP). Stapes prostheses are fixed to incus 26 and protrude by way of a piston into auris interna 40. PORP is usually lies against tympanic membrane 16, malleus 24 or incus 26 and establishes a connection with an intact stapes superstructure. TORP is usually used when the malleus 24, incus 26 and stapes 28 are absent, but the stapes footplate is intact.

Ossiculoplasty is performed under local or general anesthesia. The ear is prepped and draped in a sterile fashion. A tympanomeatal flap is elevated to expose middle ear 20 cavity and access the auditory ossicles. The auditory ossicles are inspected for any defects and gently palpated to assess for mobility and continuity. Stapes footplate mobility is essential for hearing success. If the distal portion of stapes 28, namrly stapes capitulum, is intact, then a PORP can be used. If the stapes footplate is intact and mobile, a TORP can be used.

The distance from the mobile stapes 28 superstructure or footplate to tympanic membrane 16 is measured, and the prothesis is then trimmed and/or adjusted accordingly. The headplate of the PORP or TORP can be positioned under the native or grafted tympanic membrane 16 and the other prothesis end can be connected to the intact stapes 28 superstructure or footplate. The placement of the prothesis should result in good stability and not prone to dislocation or displacement.

Illustrative embodiments of the invention are described below. In the interest of clarity, not all features of actual implementation are described in this specification. It should be appreciated that various features or elements described in the context of some embodiment may be interchangeable with features or elements of any other embodiment described in the specification. Moreover, it will be appreciated that for the development of any actual embodiment, numerous implementation-specific decisions must be made to achieve the developers' specific goals, such as compliance with technology- or business-related constraints, which may vary from one implementation to another, and the effort of such a development might be complex and time-consuming, but would nevertheless be a routine undertaking for those of ordinary skill in the art having the benefit of this disclosure.

Figures 2A, 2B:
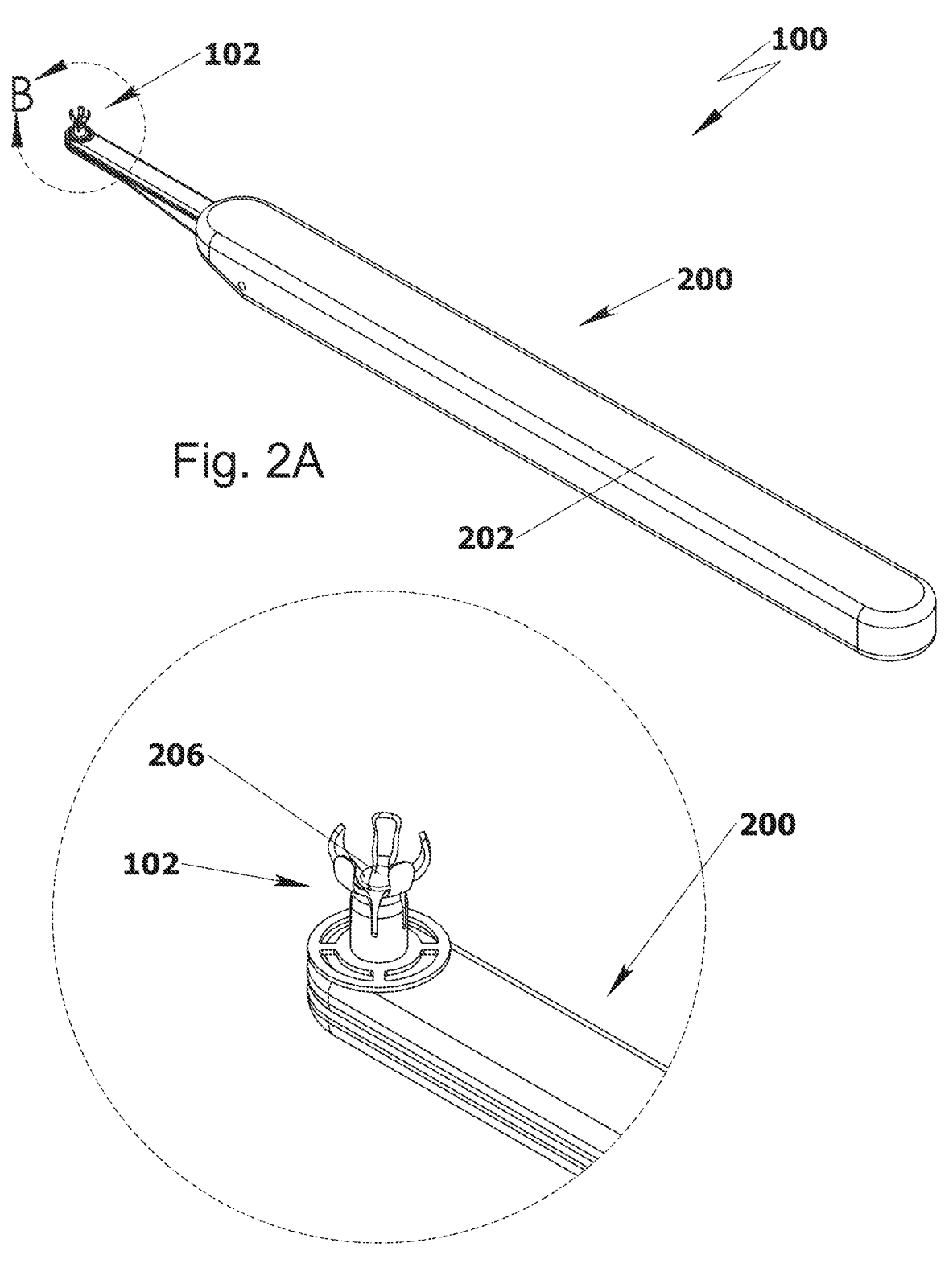
FIG. 2A is an isometric view of an embodiment of the system for partial ossicular replacement.
FIG. 2B is an isometric view of the system.

In accordance with some embodiments of the present invention, reference is now made to FIGS. 2A and 2B, showing an isometric view of system 100. System 100 is configured for partial ossicular replacement with controllable stapedial engaging function. In some embodiments, system 100 comprises partial ossicular replacement prosthesis 102, hereinafter abbreviated by acronym PORP. Partial ossicular replacement prosthesis (PORP) 102 is configured for connecting tympanic membrane 16 with a distal portion of stapes 28. In some examples, PORP 102 is configured in various lengths, widths, diameters and/or shapes.

In some example, at least a portion or part of PORP 102 is made of at least one appropriately biocompatible material, such as Nitinol, gold, tantalum, steel, platinum, titanium and/or other resilient metals and/or composite materials and/or a combination thereof. In other example, at least a portion or part of PORP 102 is made of at least one bioceramic materials, such as bioglass, glass-ceramic materials, alumina, zirconia, ceramic oxide, carbon, hydroxyapatite and/or other bioceramic materials and/or a combination thereof. In another example, at least a portion or part of PORP 102 is made of at least one biocompatible plastic, such as silicone, polyethylene, polytetrafluorethylene and/or other biocompatible plastic and/or combination thereof.

Figures 3A, 3B, 3C:
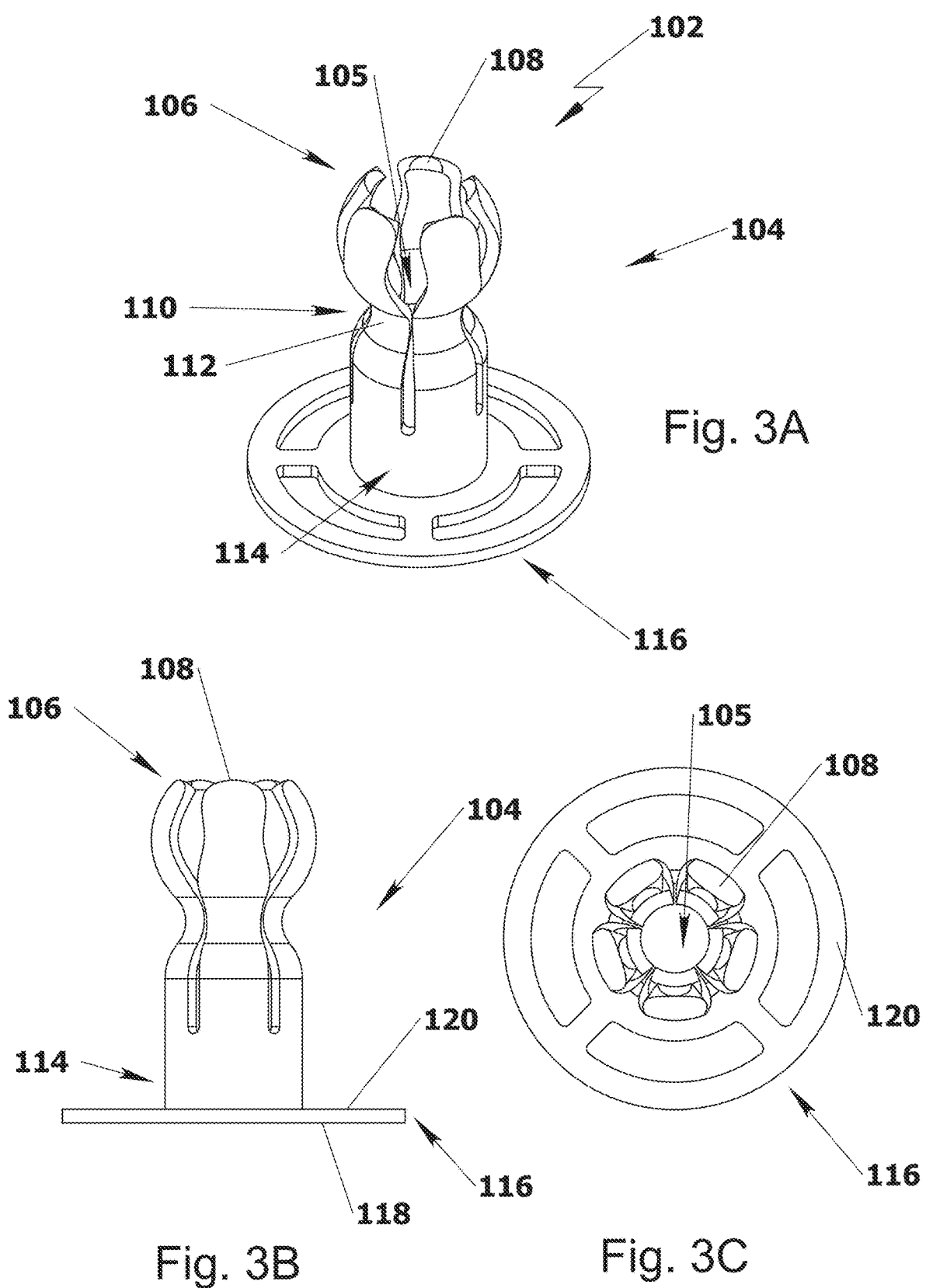
FIG. 3A is an isometric view of the partial ossicular replacement prosthesis, in a convergent configuration.
FIG. 3B is a side view of THE partial ossicular replacement prosthesis, in a convergent configuration.
FIG. 3C is a top view of THE partial ossicular replacement prosthesis, in a convergent configuration.

In some embodiments of the present invention, PORP 102 is configured to assume at least two configurations. In accordance with some embodiments, reference is now made to FIG. 3A to 3C, showing respectively isometric, side and top views of PORP 102, in a convergent configuration. In some embodiments, PORP 102 comprises stapedial part 104, as well as to FIGS. 2A and 2B. Stapedial part 104 is configured for connecting with a distal part of a stapes, such as stapes 28 shown in FIG. 1. In some embodiments, stapedial part 104 comprises an essentially cylindrical shell shape with elongated interior lumen 105. Elongated interior lumen 105 within the essentially cylindrical shell shape of stapedial part 104 is configured to accommodate plunger 206 that is manipulatable by tab 208 of applicator device 200. In some embodiments, the essentially cylindrical shell shape of stapedial part 104 is configurable at various interior and/or exterior diameters, lengths and shapes.

In some embodiments, stapedial part 104 comprises distal terminal stapedial engaging portion 106. Stapedial engaging portion 106 is configured for being readily connectable with a distal portion of stapes 28. In some embodiments, stapedial

Figures 5A, 5B:
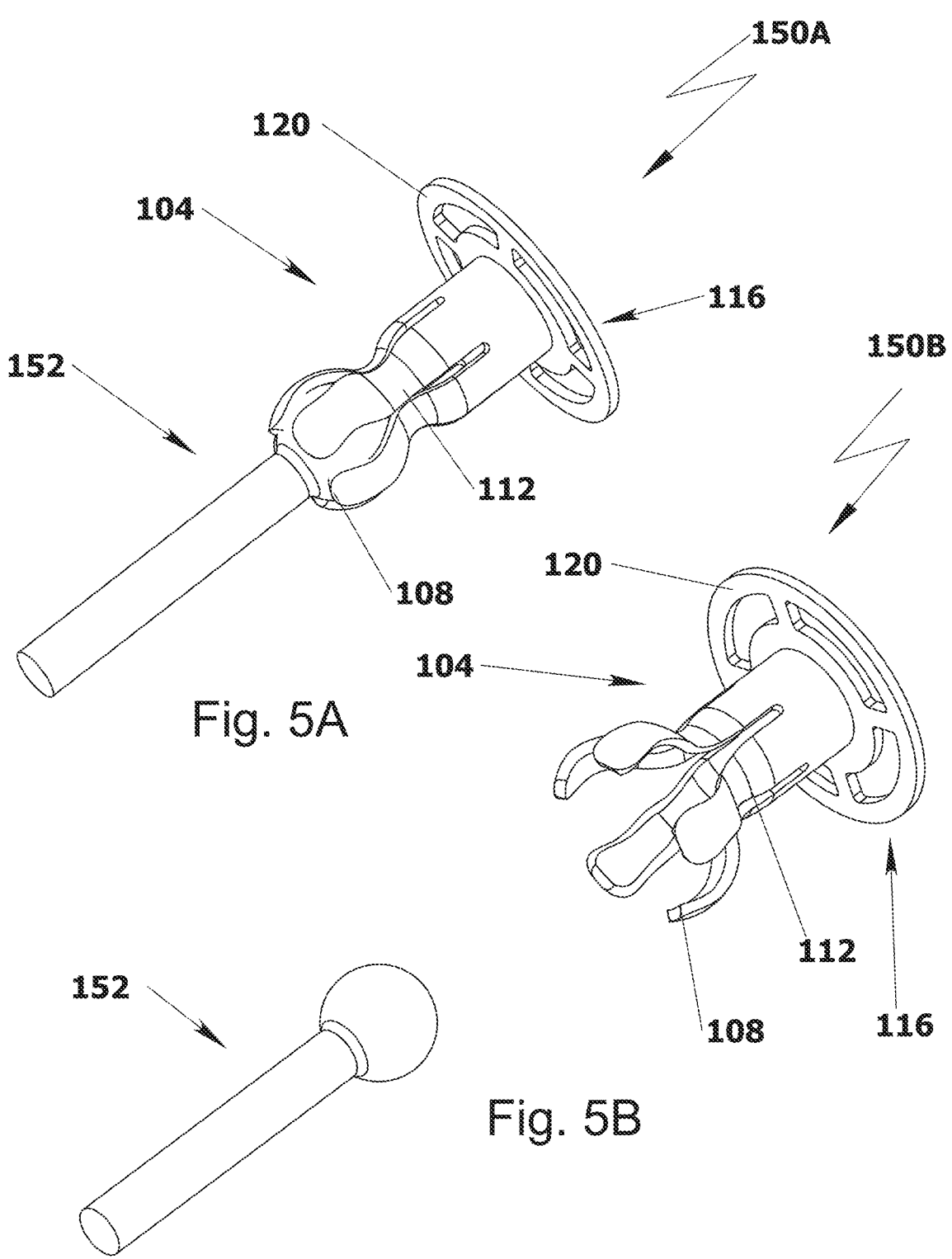
FIG. 5A is an isometric view of partial ossicular replacement prosthesis, in a convergent configuration conforms to stapes emulating structure.
FIG. 5B is an isometric view of partial ossicular replacement prosthesis, in a divergent configuration and stapes emulating structure.

13 engaging portion 106 further comprises a plurality of structured elements 108. The plurality of structured elements 108 are configured for controllably conforming to a distal portion of stapes 28. As shown in FIG. 5A, complex 150A of PORP 102 in the convergent configuration conforms to stapes emulating structure 152. In some embodiments, the plurality of structured elements 108 comprise at least one edge with a profile, such as chamfered, filleted or beveled profile.

In some embodiments, PORP 102 of system 100 is configured to assume a plurality of configurations in-between the divergent configuration and convergent configuration. In some embodiments, plunger 206 of applicator device 200 plunger is configured to be controllably withdrawn within elongated interior lumen 105 of stapedial part 104. In such embodiments, PORP 102 is configured to be gradually altered between the divergent and convergent configurations.

In some embodiments, stapedial part 104 comprises centrical applicator operated portion 110. Centrical applicator operated portion 110 forms a continuum with stapedial engaging portion 106. In some embodiments, centrical applicator operated portion 110 comprises a plurality of protruding elements 112. The plurality of protruding elements 112 face inwardly into elongated interior lumen 105 of stapedial part 104. The plurality of protruding inwardly facing elements 112 are configured to be operated by applicator 200.

In some embodiments, stapedial part 104 comprises proximal basal stem portion 114. Proximal basal stem portion 114 forms a continuum with centrical applicator operated portion 110 of stapedial part 104. Proximal basal stem portion 114 is configured for being connected with tympanic part 116 of PORP 102.

In some embodiments, PORP 102 comprises tympanic part 116. Tympanic part 116 is configured for lying vis-à-vis tympanic membrane 16. In some embodiments, tympanic part 116 typically embodies a flattened shape. In some embodiments, part 116 typically embodies a form, such as rounded, egg-shaped, oval, horseshoe-shaped, discoid and bulb shaped form. In some embodiments, tympanic part 116 comprises at least one notch 124. At least one notch 124 is configured for fitting vis-à-vis tympanic membrane 16. In some examples, at least one notch 124 comprises arcuate shape of various sizes.

In some embodiments, tympanic part 116 comprises anterior face 118. Anterior face 118 of tympanic part 116 is often directly engaged with tympanic membrane 16. In some embodiments, however, a piece of cartilage is firstly placed over anterior face 118 of tympanic part 116, and only then anterior face 118 of tympanic part 116 is covered with tympanic membrane 16.

Figure 6:
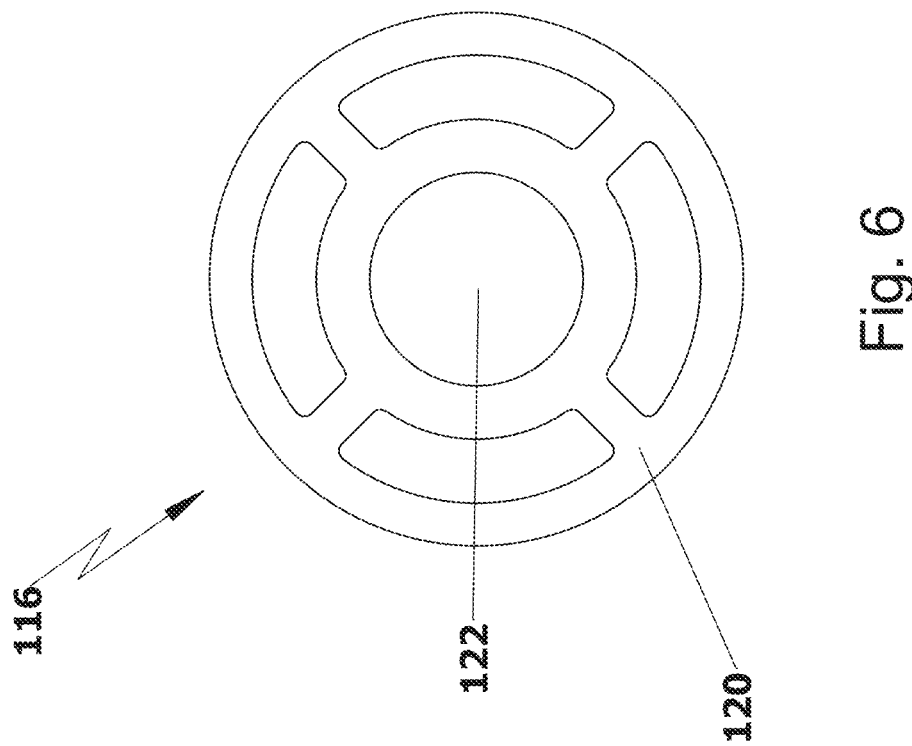
FIG. 6 is a top view of the tympanic part of the partial ossicular replacement prosthesis.
Figures 8A, 8B:
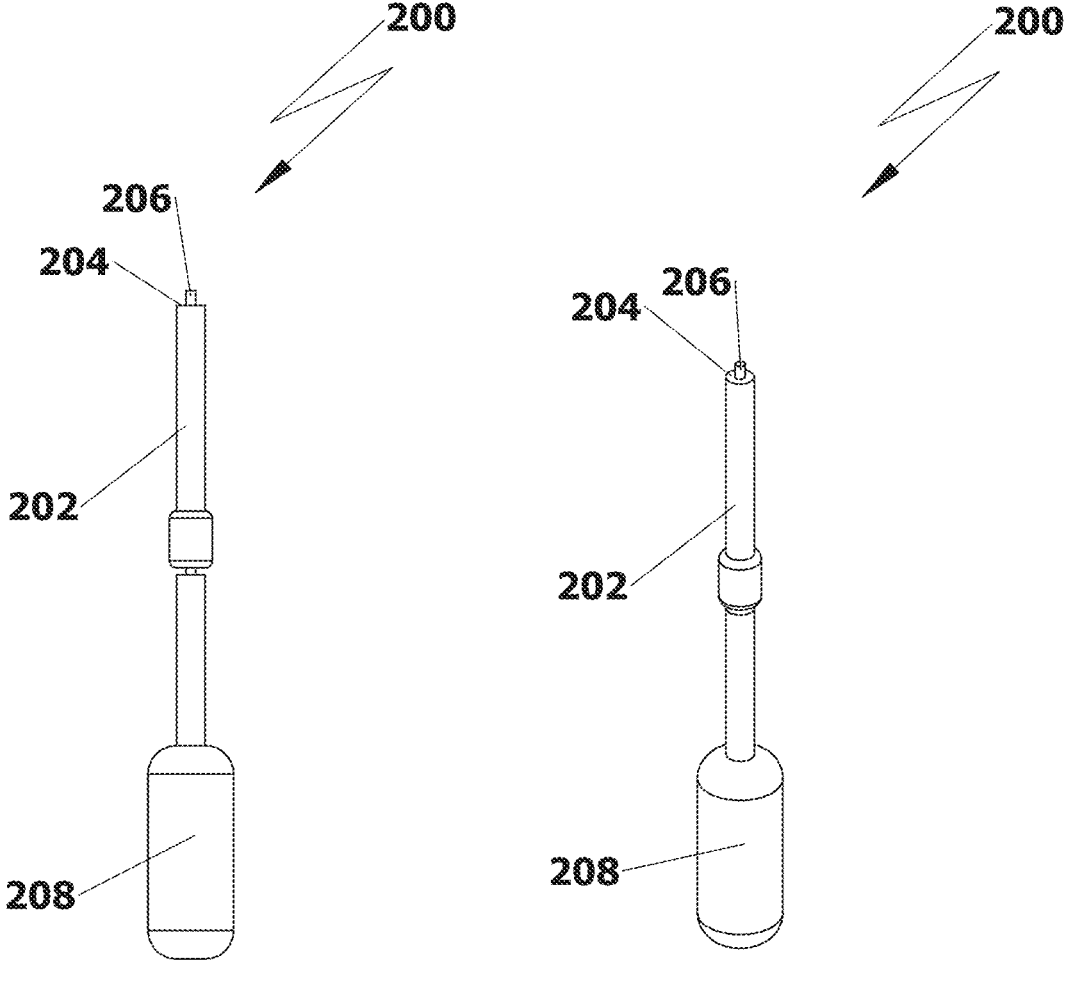
FIG. 8A is a side view of another exemplary of an applicator device.
FIG. 8B is an isometric view of another exemplary of an applicator device.

In some embodiments, tympanic part 116 comprises posterior face 120, shown in FIG. 6. Posterior face 120 of tympanic part 116 forms a continuum with proximal basal stem portion 114 of stapedial part 104. In some embodiments, anterior face 118 and/or posterior face 120 of tympanic part 116 comprise/s: a notch, groove, recess, circular aperture, structured aperture, furrowed surface, textured surface and any combination thereof.

In some embodiments, tympanic part 116 comprises throughout aperture 122, shown in FIG. 6. Throughout aperture 122 is disposed essentially at a center of the essentially flattened shape of tympanic part 116.

In some embodiments, proximal basal stem portion 114 of PORP 102 comprises a screw. The screw threading at proximal basal stem portion 114 of PORP 102 is configured for adjusting PORP 102 in length. In some embodiments, proximal basal stem portion 114 of PORP 102 comprises an external screw threading. An external screw threading is configured for matching with an internal screw threading of throughout aperture 122 of tympanic part 116 of PORP 102. In some embodiments, throughout aperture 122 comprises an internal screw threading. An internal screw threading is operatively connectable with stapedial part 104 of PORP 102.

In some embodiments of the present invention, system 100 comprises applicator device 200. In accordance with some embodiments, reference is now made to FIG. 7A to 7D and FIGS. 8A and 8B, showing respectively isometric, side, top and bottom views of applicator device 200. Applicator device 200 is configured for partial ossicular replacement with PORP 102, characterized by controllable stapedial engaging function. In some embodiments, applicator device 200 comprises handpiece 202. Handpiece 202 is configured for manual griping by the operator. In some embodiments, applicator device 200 comprises essentially planar static face 204. Planar static face 204 is configured for engaging to anterior face 118 of tympanic part 116 of PORP 102.

In some embodiments, applicator device 200 comprises an elongated essentially cylindrically shaped plunger 206. Plunger 206 is configured to be introducible into elongated interior lumen 105 of stapedial part 104 of PORP 102 through throughout aperture 122 of tympanic part 116 of PORP 102.

In some embodiments, applicator device 200 comprises tab 208. Tab 208 is operatively connected to elongated essentially cylindrically shaped plunger 206. Tab 208 is configured for controllably translating essentially cylindrically shaped plunger 206 within elongated interior lumen 105 of stapedial part 104 of PORP 102.

Figures 4A, 4B, 4C:
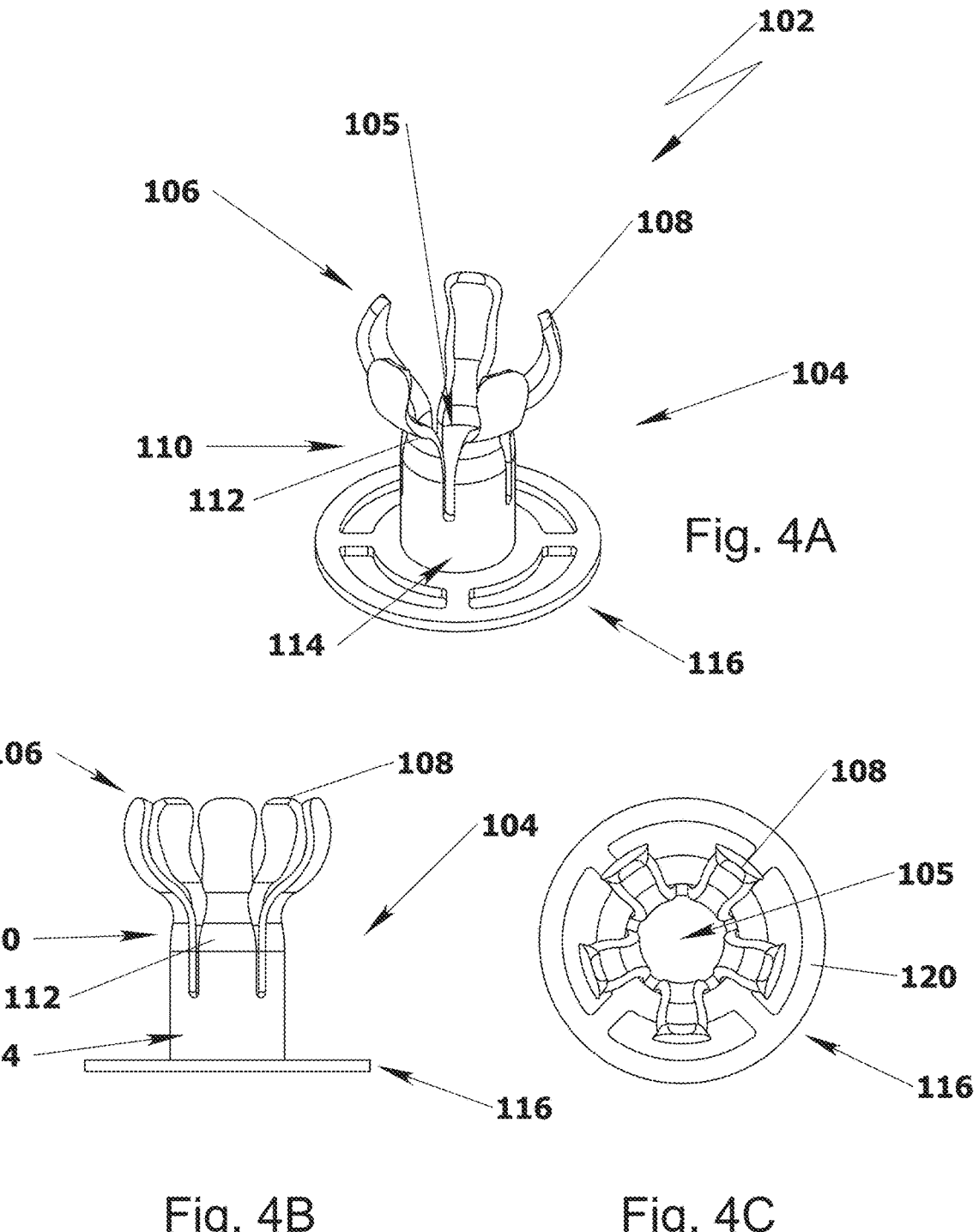
FIG. 4A is an isometric view of partial ossicular replacement prosthesis, in a divergent configuration.
FIG. 4B is a side view of partial ossicular replacement prosthesis, in a divergent configuration.
FIG. 4C is a top view of partial ossicular replacement prosthesis, in a divergent configuration.

In accordance with some embodiments, of the present invention, reference is now made to FIG. 4A to 4C, showing respectively isometric, side and top views of PORP 102, in a divergent configuration. In some embodiments, in the divergent configuration of PORP 102 the plurality of inwardly facing elements 112 of centrical portion 110 of stapedial part 102 are driven by a distal portion of plunger 206. The divergent configuration of PORP 102 further includes essentially spreading apart the plurality of structured elements 108 of distal terminal stapedial engaging portion 106 of stapedial part 104. With reference to FIG. 5B combination 150B of PORP 102 in the divergent configuration and stapes emulating structure 152 is shown.

Figures 9A, 9B:
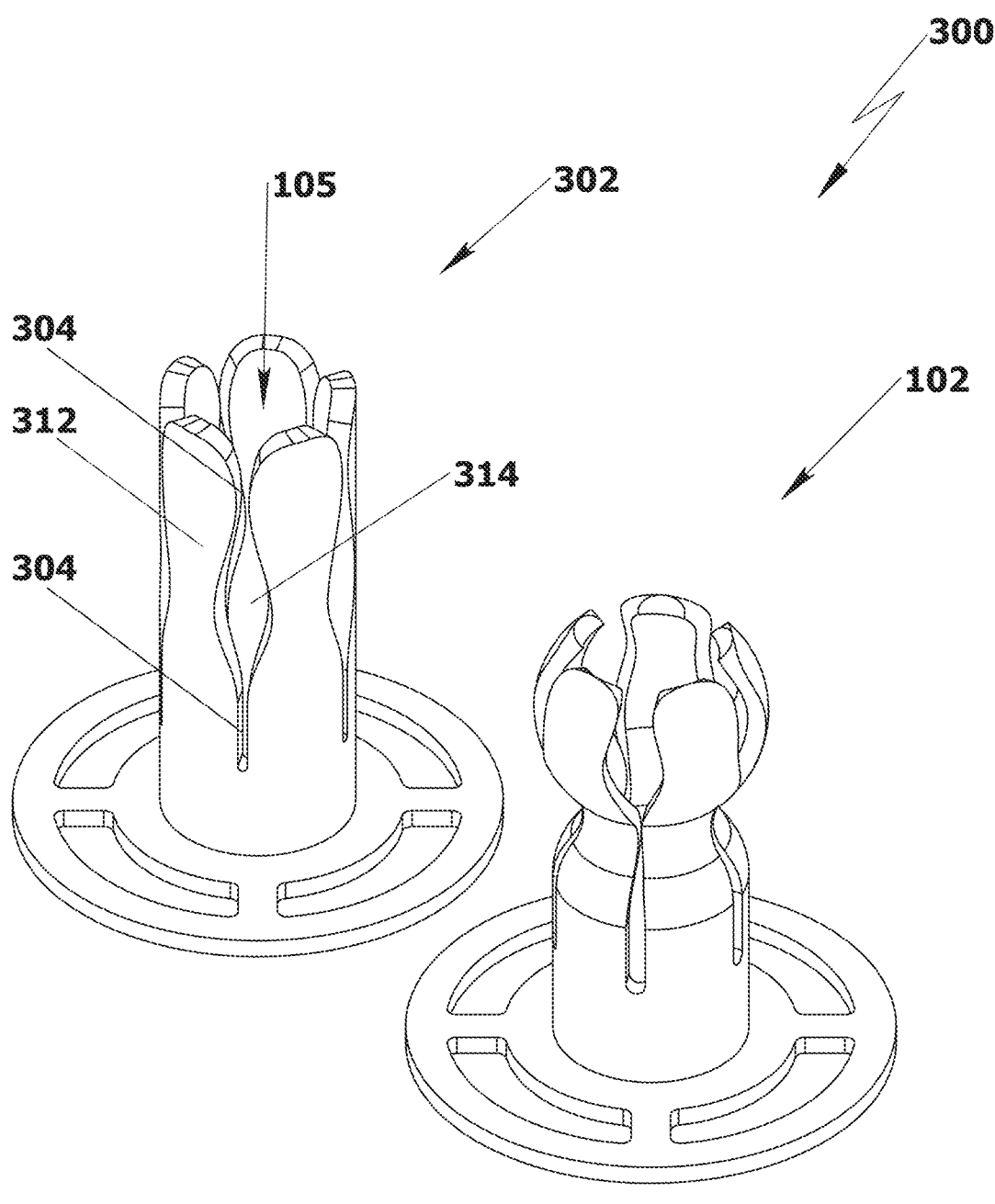
FIG. 9A is an isometric view of the stapedial part preform during the stages of manufacture of partial ossicular replacement prosthesis.
FIG. 9B is an isometric view of the stapedial part preform during the stages of manufacture of partial ossicular replacement prosthesis.
Figure 10:
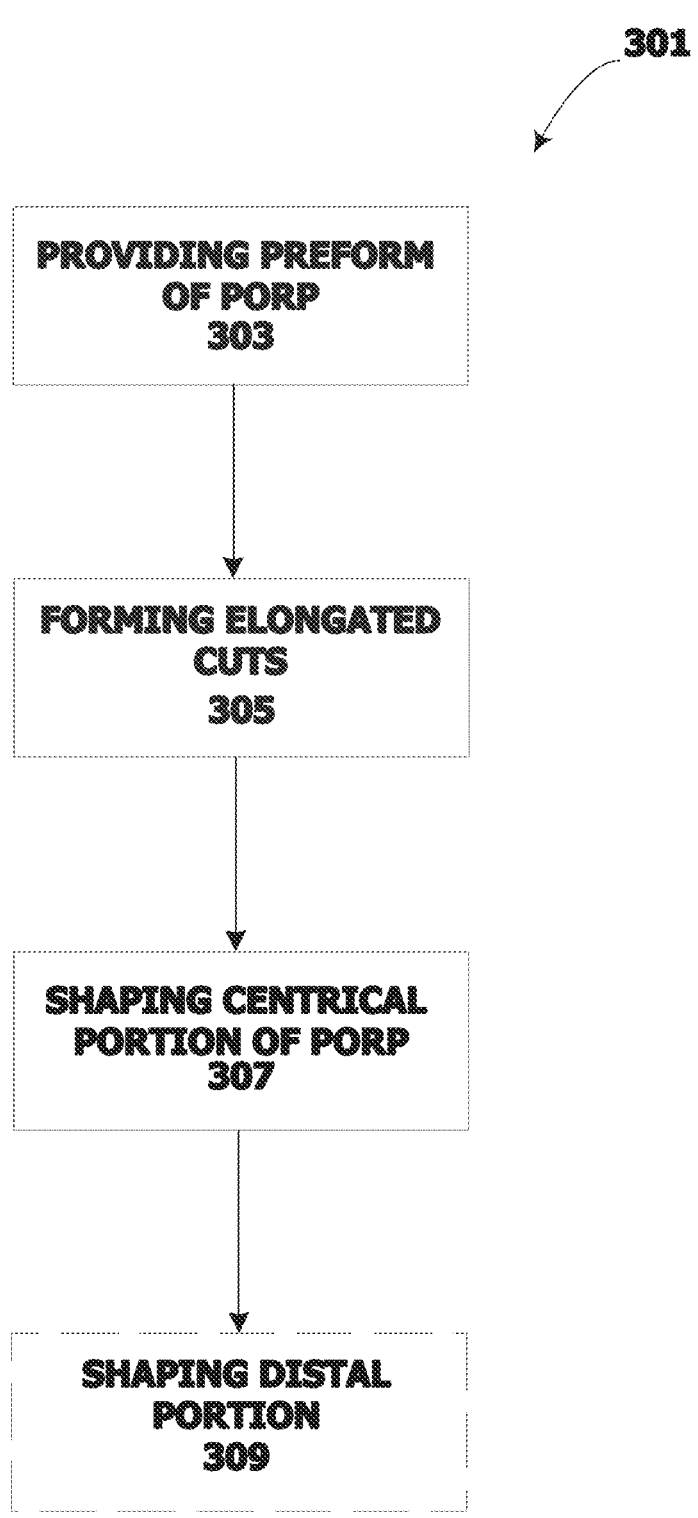
FIG. 10 is a schematic block diagram of the process of partial ossicular replacement prosthesis manufacturing.

In accordance with some embodiments of the present invention, reference is now made to FIGS. 9A and 9B showing isometric views of preform 302 comprising at least the stapedial part during the stages of manufacture of PORP 102, as well as to FIG. 10 showing schematic block diagram of process 301 of PORP 102 manufacturing. In some embodiments, process 301 of manufacturing PORP 102 involves processing preform 302 by at least one machine for producing one-part of the protheses, and/or individual parts thereof, as well as entire PORP 102, such as by a molding machine.

In some embodiments, process 301 of manufacturing PORP 102 commences at step 303 with providing preform 302 of at the least stapedial part. In some embodiments, preform 302 of at least the stapedial part comprises an essentially cylindrical shell shape with elongated interior lumen 105. In some embodiments, providing preform 302 comprises manufacturing a plurality of preforms, of different lengths, shapes and diameters.

In accordance with some embodiments of the present invention, process 301 of manufacturing PORP 102 comprises forming a plurality of elongated cuts 304, at step 305. In some embodiments, forming the plurality of elongated cuts 304 of step 305 is performed from the distal terminal face of preform 302, along a substantial length of essentially cylindrical shell shape of preform 302. In some embodiments, the plurality of elongated cuts 304 at step 305 forms a plurality of elongated biasing elements 312 extending from proximal basal stem portion 114 of an essentially cylindrical shell shape of preform 302. In some embodiments, the forming of plurality of elongated cuts 304 at step 305 includes processing preform 302 by at least one machine, such as laser cutting machine, electrical discharge machine, CNC, drills or any other type of subtractive manufacturing, as well as any combination thereof.

In accordance with some embodiments of the present invention, process 301 of manufacturing PORP 300 further comprises step 307 of shaping the centrical portion of a of elongated biasing elements 312. In some embodiments, step 307 of shaping of the centrical portion of plurality of elongated biasing elements 312 forms a plurality of protruding elements 112, such as protruding elements shown in 2A and 3A, facing inwardly into elongated interior lumen 105 of preform 302. In some embodiments, step 307 of shaping centrical portion of plurality of elongated biasing elements 312 forms centrical applicator operated portion 110 of stapedial part 104 of PORP 102. In some embodiments, step 307 of shaping the centrical portion of plurality of elongated biasing elements 312 includes processing preform 302 by at least one machine, such as a press, punching or metal bending machine.

In some preferred embodiments, process 301 of manufacturing PORP 300 yet further comprises a step of forming a plurality of mariquose shaped recesses 314, in-between elongated biasing elements 312. The step of forming a plurality of mariquose shaped recesses 314, in-between elongated biasing elements 312, is typically performed following the forming of plurality of elongated cuts 304 at step 305 and prior to step 307 of shaping centrical portion of plurality of elongated biasing elements 312.

In some embodiments, process 301 of manufacturing PORP 300 further comprises step 309 of shaping the distal terminal portion of plurality of elongated biasing elements 308. In some embodiments, step 309 of shaping the distal terminal portion of plurality of elongated biasing elements 312 forms a plurality of structured elements configured to conform to a distal portion of stapes, such as stapes 28 shown in FIG. 1. In some embodiments, step 309 of shaping the distal terminal portion of the plurality of biasing elements 312 forms stapedial engaging portion 106 of stapedial part 104. In some embodiments, shaping a distal terminal portion of the plurality of biasing elements 308 includes processing by at least one machine such, as a chamfering and/or filleting machine.

Figure 11:
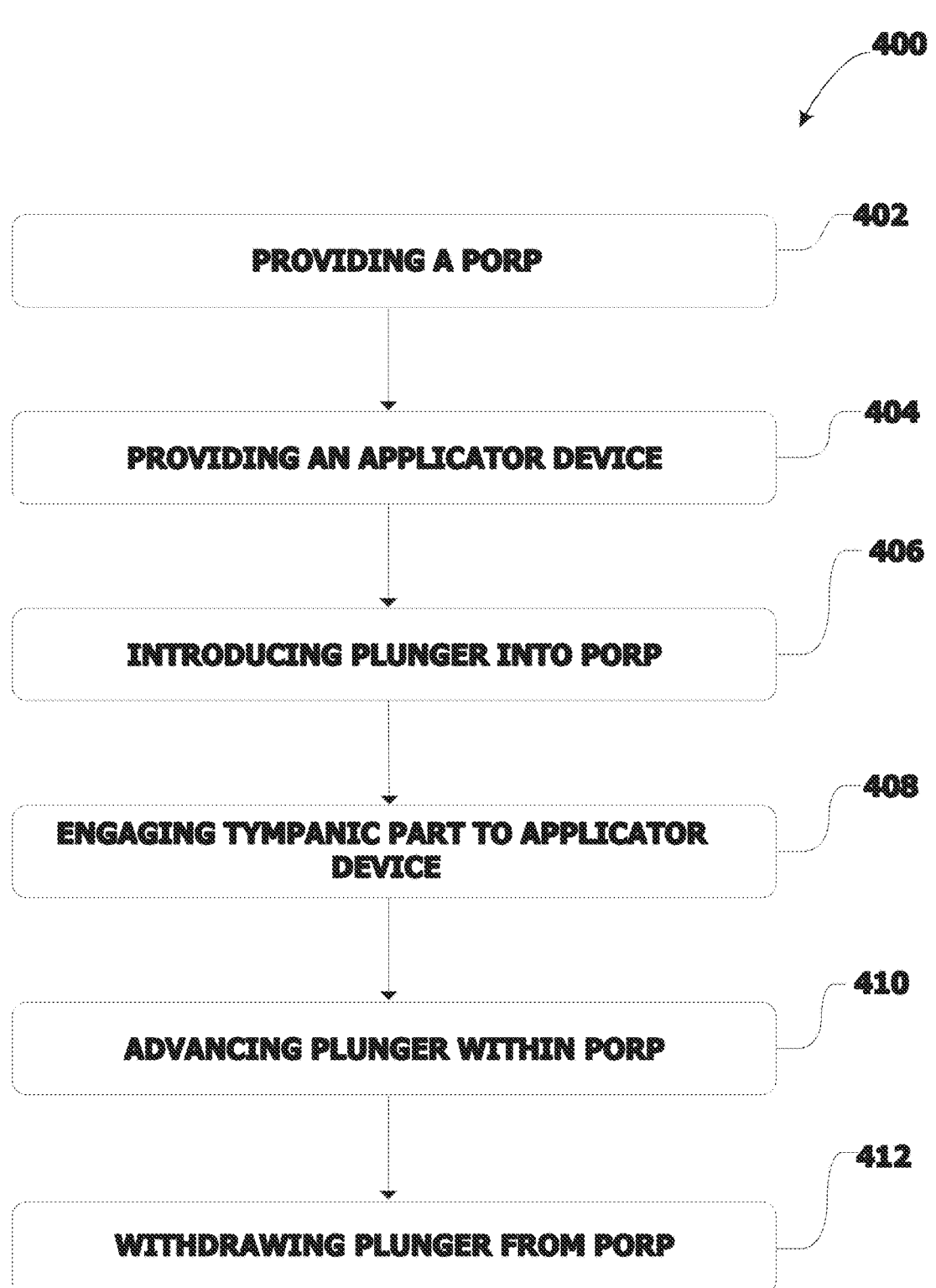
FIG. 11 is a high-level flowchart of the method of operating an applicator device for implanting the partial ossicular replacement prosthesis.

In accordance with some aspects of the present invention, reference is now made to FIG. 11, showing a high-level flowchart of method 400 of operating an applicator device for manipulating the PORP, such as applicator device 200 for manipulating PORP 102 shown in 2A and 2B. In some examples, method 400 of operating applicator 200 device for manipulating PORP 102 commences at step 402, with providing suitable PORP 102. In some examples, step 402, of providing PORP 102, comprises selecting PORP 102 with diameter, length and/or shape suitable for specific patient, from a kit comprising a plurality of PORPs with different diameters, lengths and/or shapes. In some examples, step

402, of providing PORP 102, comprises selecting PORP 102 with size, length, diameter and/or shape matching plunger 206 of applicator device 200. In some examples, step 402, of providing a PORP, comprises length adjustment of stapedial part 104 of PORP 102. In some examples, step 402, of providing a PORP, includes using disinfectants, sterilization, as well as providing of instruments and utensils for proper handling, such as tweezers, scissors and/or forceps.

In some embodiments, method 400 of operating an applicator device for a PORP comprises step 404, of providing an applicator device. In some examples, step 404 of providing an applicator device, comprises using disinfectants and/or sterilization of applicator device 200. In some examples, step 404 of providing an applicator device, comprises length adjustment of plunger 206 of applicator device 200. In some examples, step 404, of providing an applicator device, comprises selecting plunger 206 of applicator device 200 with size, length, diameter and/or shape matching PORP 102.

In some embodiments, method 400 of operating an applicator device for a PORP comprises step 406, of introducing plunger 206 into an elongated interior lumen of the stapedial part of a PORP. In some examples, step 406, of introducing the plunger of applicator device into the elongated interior lumen of the stapedial part, is performed by manipulating PORP by sterile instruments, such as forceps.

In some embodiments, method 400 of operating an applicator device for a PORP comprises step 408, of engaging the anterior face of the tympanic part of the PORP to the essentially planar static face of the applicator device. Step 408 is configured for stabilizing the engaging of PORP 102 by applicator device 200 onto the stapes.

In some embodiments, method 400 of operating an applicator device for a PORP comprises step 410 of advancing the plunger of an applicator device within an elongated interior lumen of the stapedial part of the PORP. In some examples, step 410 is configured for driving PORP into the divergent configuration. In some examples, step 410 is performed by pressing onto tab 208 of applicator device 200.

In some embodiments, method 400 of operating an applicator device for a PORP comprises step 412 of withdrawing the plunger of an applicator device from the plurality of inwardly facing elements of a stapedial part of the PORP. In some examples, step 412 of withdrawing the plunger of an applicator device from the plurality of inwardly facing elements of a stapedial part of the PORP is configured for driving PORP 102 into the convergent configuration on a distal portion of stapes 28. In some examples, step 412 is performed by gradually pulling tab 208 of applicator device 200 or by releasing tab 208 of applicator device 200.

It will be appreciated by persons skilled in the art that the present invention is not limited by what has been particularly shown and described herein above. Rather the scope of the invention is defined by the claims which follow:

The invention claimed is:

1. A system for partial ossicular replacement with controllable stapedial engaging function comprises:
    (a) a partial ossicular replacement prosthesis comprising:
        (I) a stapedial part comprising an essentially cylindrical shell shape with an elongated interior lumen, said stapedial part comprising:
            (i) a distal terminal stapedial engaging portion comprising a plurality of structured elements configured for controllably conforming to a distal portion of a stapes;
            (ii) a centrical applicator operated portion, forming a continuum with said stapedial engaging portion, comprising a plurality of protruding elements facing inwardly into said elongated interior lumen of said stapedial part, wherein said plurality of protruding elements are configured to be operated by an applicator;

(iii) a proximal basal stem portion, forming a continuum with said centrical portion;

(II) a tympanic part comprising an essentially flattened shape, said tympanic part comprising:

(i) an anterior face, associated with a tympanic membrane;

(ii) a posterior face, forming a continuum with said proximal basal stem portion;

(iii) a throughout aperture, disposed essentially at a center of said essentially flattened shape;

(b) an applicator device for said partial ossicular replacement prosthesis comprising:

(I) a handpiece configured for manual grip by an operator;

(II) an essentially planar static face, configured to engage to said anterior face of said tympanic part of said partial ossicular replacement prosthesis;

(III) an elongated essentially cylindrically shaped plunger, configured to be introducible into said elongated interior lumen of said stapedial part of said partial ossicular replacement prosthesis, through said throughout aperture in said tympanic part of said partial ossicular replacement prosthesis;

(IV) a tab operatively connected to said elongated essentially cylindrically shaped plunger, configured for controllably translating said essentially cylindrically shaped plunger within said elongated interior lumen of said stapedial part of said partial ossicular replacement prosthesis;

wherein said partial ossicular replacement prosthesis is configured to assume at least two configurations:

(i) a divergent configuration in which a distal portion of said plunger is engaged to said plurality of protruding elements of said centrical portion of said stapedial part; whereby said plurality of said structured elements of said distal terminal stapedial engaging portion of said stapedial part are essentially spread apart, and (ii) a convergent configuration in which said distal portion of said plunger is withdrawn from said plurality of protruding elements of said centrical portion of said stapedial part; whereby said plurality of said structured elements of said distal terminal stapedial engaging portion of said stapedial part essentially conform to said distal portion of said stapes.

2. The system as in claim 1, wherein said partial ossicular replacement prosthesis is configured to assume a plurality of configurations in-between said divergent configuration and said convergent configuration.

3. The system as in claim 1, wherein said plunger is configured to be controllably withdrawn within said elongated interior lumen of said stapedial part, whereby said partial ossicular replacement prosthesis is configured to be gradually altered between said divergent and said convergent configurations.

4. The system as in claim 1, wherein said partial ossicular replacement prosthesis comprises at least one biocompatible material selected from a group of: a pliable or pliant metal, pliable or pliant alloy, bio-ceramic material, plastic resilient and any combination thereof.

5. The system as in claim 1, wherein said partial ossicular replacement prosthesis further comprises a plurality of partial ossicular replacement prostheses, wherein said essentially cylindrical shell shape with said elongated interior lumen of said stapedial part of each one of said plurality of said partial ossicular replacement prostheses comprises at least one different parameter selected from the group consisting of: a length, diameter and shape.

6. The system as in claim 1, wherein at least one edge of said plurality of structured elements of said stapedial engaging portion of said stapedial part of said partial ossicular replacement prosthesis comprises a profile selected from a group of: a chamfered profile, filleted profile or beveled profile.

7. The system as in claim 1, wherein said tympanic part of said partial ossicular replacement prosthesis comprises at least one shape selected from a group of: a discoid shape, egg shape, oval shape, bulb shaped and horseshoe shape.

8. The system as in claim 1, wherein said tympanic part of said partial ossicular replacement prosthesis comprises at least one structural element selected from a group of: a notch, groove, recess, circular aperture, structured aperture, furrowed surface and textured surface.

9. The system as in claim 1, wherein said proximal basal stem portion of said stapedial part of said partial ossicular replacement prosthesis comprises external screw threading matching an internal screw threading of said throughout aperture of said tympanic part of said partial ossicular replacement prosthesis, wherein said stapedial part of said partial ossicular replacement is configured for length adjustment.

10. The system as in claim 1, wherein said plunger forms a perpendicular arrangement with said tab of said applicator device for said partial ossicular replacement prosthesis.

11. A partial ossicular replacement prosthesis with controllable stapedial engaging function comprising:

(a) a stapedial part comprising an essentially cylindrical shell shape with an elongated interior lumen, said stapedial part comprising:

(I) a distal terminal stapedial engaging portion comprising a plurality of structured elements configured for controllably conforming to a distal portion of a stapes;

(II) a centrical applicator operated portion, forming a continuum with said stapedial (II) engaging portion, comprising a plurality of protruding elements facing inwardly into said elongated interior lumen of said stapedial part, wherein said plurality of protruding elements are configured to be operated by an applicator;

(III) a proximal basal stem portion, forming a continuum with said centrical portion;

(b) a tympanic part comprising an essentially flattened shape, said tympanic part comprising:

(I) an anterior face, associated with a tympanic membrane;

(II) a posterior face, forming a continuum with said proximal basal stem portion;

(III) a throughout aperture, disposed essentially at a center of said essentially flattened shape;

wherein said partial ossicular replacement prosthesis is configured to assume at least two configurations:

(i) a divergent configuration in which a distal portion of a plunger of said applicator is engaged to said plurality of protruding elements of said centrical portion of said stapedial part; whereby said plurality of said structured elements of said distal terminal stapedial engaging portion of said stapedial part are essentially spread apart, and (ii) a convergent configuration in which said distal portion of said plunger of said applicator is withdrawn from said plurality of protruding elements of said centrical portion of said stapedial part; whereby said plurality of said structured elements of said distal terminal stapedial engaging portion of said stapedial part essentially conform to said distal portion of said stapes.

12. The partial ossicular replacement prosthesis, as in claim 11, wherein said partial ossicular replacement prosthesis is configured to assume a plurality of configurations in-between said divergent configuration and said convergent configuration.

13. The partial ossicular replacement prosthesis, as in claim 11, wherein said plunger of said applicator device is configured to be controllably withdrawn within said elongated interior lumen of said stapedial part, whereby said partial ossicular replacement prosthesis is configured to be gradually altered between said divergent and said convergent configurations.

14. The partial ossicular replacement prosthesis, as in claim 11, wherein said partial ossicular replacement prosthesis comprises at least one biocompatible material selected from a group of: a pliable or pliant metal, pliable or pliant alloy, bio-ceramic material, plastic resilient and any combination thereof.

15. The partial ossicular replacement prosthesis, as in claim 11, wherein said partial ossicular replacement prosthesis further comprises a plurality of partial ossicular replacement prostheses, wherein said essentially cylindrical shell shape with said elongated interior lumen of said stapedial part of each one of said plurality of said partial ossicular replacement prostheses comprises at least one different parameter selected from the group consisting of: a length, diameter and shape.

16. The partial ossicular replacement prosthesis, as in claim 11, wherein at least one edge of said plurality of structured elements of said stapedial engaging portion of said stapedial part of said partial ossicular replacement prosthesis comprises a profile selected from a group of: a chamfered profile, filleted profile or beveled profile.

17. The partial ossicular replacement prosthesis, as in claim 11, wherein said tympanic part of said partial ossicular replacement prosthesis comprises at least one shape selected from a group of: a discoid shape, egg shape, oval shape, bulb shaped and horseshoe shape.

18. The partial ossicular replacement prosthesis, as in claim 11, wherein said tympanic part of said partial ossicular replacement prosthesis comprises at least one structural element selected from a group of: a notch, groove, recess, circular aperture, structured aperture, furrowed surface and textured surface.

19. The partial ossicular replacement prosthesis, as in claim 11, wherein said proximal basal stem portion of said stapedial part of said partial ossicular replacement prosthesis comprises external screw threading matching an internal screw threading of said throughout aperture of said tympanic part of said partial ossicular replacement prosthesis, wherein said stapedial part of said partial ossicular replacement is configured for length adjustment.

\* \* \* \* \*